(12) United States Patent
Mazanec

(10) Patent No.: US 11,633,591 B2
(45) Date of Patent: Apr. 25, 2023

(54) COMBINATION IMPLANT SYSTEM WITH REMOVABLE EARPLUG SENSOR AND IMPLANTED BATTERY

(71) Applicant: Envoy Medical Corporation, White Bear Lake, MN (US)

(72) Inventor: Paul R. Mazanec, Ham Lake, MN (US)

(73) Assignee: Envoy Medical Corporation, White Bear Lake, MN (US)

( * ) Notice: Subject to any disclaimer, the term of this patent is extended or adjusted under 35 U.S.C. 154(b) by 161 days.

(21) Appl. No.: 17/182,469

(22) Filed: Feb. 23, 2021

(65) Prior Publication Data

US 2022/0266002 A1    Aug. 25, 2022

(51) Int. Cl.
*A61N 1/378* (2006.01)
*A61N 1/05* (2006.01)
*A61N 1/36* (2006.01)

(52) U.S. Cl.
CPC ....... *A61N 1/0541* (2013.01); *A61N 1/36038* (2017.08); *A61N 1/3787* (2013.01)

(58) Field of Classification Search
CPC .............. A61N 1/0541; A61N 1/36038; A61N 1/3787; A61N 1/378
See application file for complete search history.

(56) References Cited

U.S. PATENT DOCUMENTS

| | | | |
|---|---|---|---|
| 2,827,041 | A | 3/1958 | Pierson |
| 4,400,590 | A | 8/1983 | Michelson |
| 4,495,384 | A | 1/1985 | Scott et al. |
| 4,729,366 | A | 3/1988 | Schaefer |
| 4,850,962 | A | 7/1989 | Schaefer |

(Continued)

FOREIGN PATENT DOCUMENTS

| | | |
|---|---|---|
| CN | 104394930 A | 3/2015 |
| CN | 110086237 A | 8/2019 |

(Continued)

OTHER PUBLICATIONS

International Patent Application No. PCT/US2022/017144, International Search Report and Written Opinion dated May 27, 2022, 16 pages.

(Continued)

*Primary Examiner* — Tammie K Marlen
(74) *Attorney, Agent, or Firm* — Fredrikson & Byron, P.A.

(57) ABSTRACT

Cochlear implant systems can comprise an implantable subsystem comprising a cochlear electrode, a stimulator, a battery, and a first near field communication interface positioned subcutaneously proximate an ear canal. Cochlear implant systems can further comprise a removable earplug comprising a sensor, a second near field communication interface, and a signal processor. The removable earplug can be inserted into an ear canal to align the first and second near field communication interfaces. Once aligned, the battery can provide electrical power to the removable earplug via the near field communication interfaces. The signal processor can receive input signals from the sensor of the removable earplug and generate a stimulation signal representative of the auditory signals. The signal processor can communicate the stimulation signal to the stimulator via the near field communication interfaces.

22 Claims, 7 Drawing Sheets

(56) References Cited

U.S. PATENT DOCUMENTS

| | | |
|---|---|---|
| 4,918,745 A | 4/1990 | Hutchison |
| 5,540,095 A | 7/1996 | Sherman et al. |
| 5,762,583 A | 6/1998 | Adams et al. |
| 6,195,585 B1 | 2/2001 | Karunasiri et al. |
| 6,212,431 B1 | 4/2001 | Hahn et al. |
| 6,259,951 B1 | 7/2001 | Kuzma et al. |
| 6,272,382 B1 | 8/2001 | Faltys et al. |
| 6,308,101 B1 | 10/2001 | Faltys et al. |
| 6,358,281 B1 | 3/2002 | Berrang et al. |
| 6,556,870 B2 | 4/2003 | Zierhofer et al. |
| 7,225,028 B2 | 5/2007 | Della Santina et al. |
| 7,319,906 B2 | 1/2008 | Kuzma et al. |
| 7,376,563 B2 | 5/2008 | Leysieffer et al. |
| 7,524,278 B2 | 4/2009 | Madsen et al. |
| 8,554,329 B1 | 10/2013 | Mann et al. |
| 8,655,449 B2 | 2/2014 | Haller et al. |
| 9,504,076 B2 | 11/2016 | El-Hoiydi et al. |
| 9,539,430 B2 | 1/2017 | Mishra et al. |
| 9,716,952 B2 | 7/2017 | Mauger |
| 9,802,043 B2 | 10/2017 | Von Ilberg |
| 10,561,335 B2 | 2/2020 | Nielsen et al. |
| 11,418,897 B2 | 8/2022 | Oplinger et al. |
| 2002/0039425 A1 | 4/2002 | Burnett et al. |
| 2002/0099421 A1 | 7/2002 | Goldsmith et al. |
| 2004/0230254 A1* | 11/2004 | Harrison ............ A61N 1/36038 607/57 |
| 2005/0033384 A1 | 2/2005 | Sacha |
| 2005/0197677 A1 | 9/2005 | Stevenson |
| 2006/0122664 A1 | 6/2006 | Sacha et al. |
| 2006/0183965 A1 | 8/2006 | Kasic, II et al. |
| 2008/0195179 A1 | 8/2008 | Quick |
| 2008/0300658 A1 | 12/2008 | Meskens |
| 2009/0018616 A1 | 1/2009 | Quick et al. |
| 2009/0082831 A1 | 3/2009 | Paul et al. |
| 2009/0187233 A1 | 7/2009 | Stracener |
| 2009/0192565 A1 | 7/2009 | Lee et al. |
| 2010/0030012 A1 | 2/2010 | Meskens |
| 2010/0042183 A1 | 2/2010 | Beck |
| 2010/0317913 A1 | 12/2010 | Conn et al. |
| 2011/0082521 A1 | 4/2011 | Botros et al. |
| 2011/0116669 A1 | 5/2011 | Karunasir |
| 2011/0137180 A1 | 6/2011 | Johnson et al. |
| 2011/0144719 A1 | 6/2011 | Perkins et al. |
| 2011/0160808 A1 | 6/2011 | Lyden et al. |
| 2011/0280426 A1 | 11/2011 | Bachler |
| 2011/0295331 A1 | 12/2011 | Wells et al. |
| 2012/0215285 A1 | 8/2012 | Tahmasian et al. |
| 2012/0277835 A1 | 11/2012 | Della Santina et al. |
| 2013/0018216 A1 | 1/2013 | Beckerle et al. |
| 2013/0023953 A1 | 1/2013 | van den Honert |
| 2013/0193914 A1 | 8/2013 | Gaddam et al. |
| 2013/0223664 A1 | 8/2013 | Meskens et al. |
| 2013/0238055 A1 | 9/2013 | Marnfeldt et al. |
| 2013/0268025 A1 | 10/2013 | Ranu |
| 2013/0278226 A1 | 10/2013 | Cong et al. |
| 2013/0317584 A1 | 11/2013 | Stevenson et al. |
| 2014/0058482 A1 | 2/2014 | Gupta et al. |
| 2014/0247954 A1 | 9/2014 | Hall et al. |
| 2014/0270211 A1 | 9/2014 | Solum et al. |
| 2014/0275730 A1 | 9/2014 | Lievens et al. |
| 2014/0309712 A1 | 10/2014 | Masaki et al. |
| 2014/0350652 A1 | 11/2014 | Suwito |
| 2015/0125012 A1 | 5/2015 | Sabin |
| 2015/0174416 A1 | 6/2015 | Angara et al. |
| 2015/0224312 A1 | 8/2015 | Platz et al. |
| 2015/0256945 A1 | 9/2015 | Mazanec |
| 2015/0374988 A1 | 12/2015 | Laudanski |
| 2015/0375003 A1 | 12/2015 | Meskens |
| 2016/0227333 A1 | 8/2016 | Babico |
| 2017/0043162 A1 | 2/2017 | Lopez-Poveda |
| 2017/0077938 A1 | 3/2017 | Heubi |
| 2017/0094396 A1 | 3/2017 | Chandramohan et al. |
| 2017/0161449 A1 | 6/2017 | Meskens |
| 2017/0259072 A1 | 9/2017 | Newham et al. |
| 2017/0360364 A1 | 12/2017 | Heasman et al. |
| 2018/0028811 A1 | 2/2018 | Van Gerwen et al. |
| 2018/0028827 A1 | 2/2018 | Schilling et al. |
| 2018/0041848 A1 | 2/2018 | Nielsen et al. |
| 2018/0050197 A1 | 2/2018 | Mazanec et al. |
| 2018/0050198 A1 | 2/2018 | Mazanec et al. |
| 2018/0050203 A1 | 2/2018 | Mazanec et al. |
| 2018/0059870 A1 | 3/2018 | Krah |
| 2018/0264269 A1 | 9/2018 | Meadows |
| 2018/0317027 A1 | 11/2018 | Bolner et al. |
| 2018/0333577 A1 | 11/2018 | Nygard et al. |
| 2018/0361151 A1 | 12/2018 | Ridler et al. |
| 2019/0045308 A1 | 2/2019 | Chen et al. |
| 2019/0046116 A1 | 2/2019 | Shah et al. |
| 2019/0217104 A1* | 7/2019 | Perkins ............ A61N 1/36038 |
| 2020/0054877 A1 | 2/2020 | Calixto et al. |
| 2020/0238075 A1 | 7/2020 | Mazanec et al. |
| 2020/0269034 A1 | 8/2020 | Mazanec et al. |
| 2020/0269035 A1 | 8/2020 | Mazanec et al. |
| 2020/0269047 A1 | 8/2020 | Mazanec et al. |
| 2020/0269048 A1 | 8/2020 | Mazanec et al. |
| 2020/0269057 A1 | 8/2020 | Mazanec et al. |
| 2020/0269058 A1 | 8/2020 | Mazanec et al. |
| 2021/0084417 A1 | 3/2021 | Bagazov et al. |
| 2021/0135704 A1 | 5/2021 | El-Hoiydi et al. |
| 2021/0187293 A1 | 6/2021 | Friedling |
| 2021/0361194 A1 | 11/2021 | Arab et al. |

FOREIGN PATENT DOCUMENTS

| | | |
|---|---|---|
| DE | 4419070 A1 | 12/1994 |
| DE | 60107062 T2 | 11/2005 |
| DE | 102013214049 B4 | 3/2015 |
| EP | 1043914 A2 | 10/2000 |
| EP | 1683544 B1 | 11/2010 |
| EP | 2884766 B1 | 2/2018 |
| EP | 3120579 B1 | 2/2020 |
| TW | 201142830 A | 12/2011 |
| WO | 2007137032 A2 | 11/2007 |
| WO | 2010056768 A1 | 5/2010 |
| WO | 2014037888 A1 | 3/2014 |
| WO | 2015077773 A1 | 5/2015 |
| WO | 2016122606 A1 | 8/2016 |
| WO | 2017100866 A1 | 6/2017 |
| WO | 2018035329 A1 | 2/2018 |
| WO | 2018144732 A1 | 8/2018 |
| WO | 2020172500 A1 | 8/2020 |

OTHER PUBLICATIONS

Mazanec et al., unpublished U.S. Appl. No. 17/006,467, entitled Programming of Cochlear Implant Accessories, filed Aug. 28, 2020, 74 pages.

Mazanec et al., unpublished U.S. Appl. No. 17/109,303, entitled Implantable Cochlear System With Inner Ear Sensor, filed Dec. 2, 2020, 54 pages.

Mazanec et al., unpublished U.S. Appl. No. 17/109,304, entitled Combination Hearing Aid and Cochlear Implant System, filed Dec. 2, 2020, 55 pages.

Mazanec et al., unpublished U.S. Appl. No. 17/109,305, entitled Cochlear Implant Stimulation Calibration, filed Dec. 2, 2020, 53 pages.

* cited by examiner

COMBINATION IMPLANT SYSTEM WITH REMOVABLE EARPLUG SENSOR AND IMPLANTED BATTERY

BACKGROUND

A cochlear implant is an electronic device that may be at least partially implanted surgically into the cochlea, the hearing organ of the inner ear, to provide improved hearing to a patient. Cochlear implants may include components that are worn externally by the patient and components that are implanted internally in the patient.

Some cochlear implant systems include an external component that contains one or more system components and a battery to power such components. Such systems can generate signals outside of the body and communicate the signals to an implanted system component. In some cases, such an external component may be size-limited, for example, in order to fit in an ear canal of a wearer.

SUMMARY

Some aspects of the present disclosure are generally directed toward cochlear implant systems. In some embodiments, a cochlear implant system comprises an implantable subsystem and a removable earplug which is configured to be inserted into an ear canal. The implantable subsystem can comprise a cochlear electrode, a stimulator in electrical communication with the cochlear electrode, and a battery in electrical communication with the stimulator. Further, the implantable subsystem can comprise a first near field communication interface in electrical communication with the battery and the stimulator. The first near field communication interface can be configured to be implanted subcutaneously, proximate an ear canal. The removable earplug of the cochlear implant system can comprise a sensor configured to sense auditory signals and generate an input signal representative of the sensed auditory signals. The removable earplug can further comprise a second near field communication interface and a signal processor in electrical communication with the sensor and the second near field communication interface.

The signal processor of the removable earplug can be configured to receive the input signal from the sensor and generate a stimulation signal based on the received input signal. When the removable earplug is inserted into the ear canal, the first near field communication interface and the second near field communication interface can be positioned proximate each other and establish a communication link therebetween. The battery can be configured to provide electrical power to the removable earplug via the communication link. Additionally, the signal processor can be configured to communicate the stimulation signal from the removable earplug to the stimulator via the communication link.

In some cases, powering components of the removable earplug via the communication link can allow for a battery having a larger capacity compared to a battery that can fit inside a removable earplug.

Some aspects of the present disclosure are generally directed toward a removable earplug configured to be inserted into an ear canal. The removable earplug can comprise a sensor configured to receive auditory signals and generate an input signal representative of the received auditory signals. The removable earplug can further comprise a signal processor in electrical communication with the sensor and configured to receive signals from the sensor and output a stimulation signal. Additionally, the removable earplug can comprise a near field communication interface in electrical communication with the sensor and the signal processor. The removable earplug may not include a power source and can be configured to receive electrical power via the near field communication interface. The removable earplug can further be configured to output the stimulation signal from the signal processor via the near field communication interface. In some embodiments, the removable earplug does not include a battery and is powered by receiving electrical power via the near field communication interface.

Some aspects of the present disclosure are generally directed toward a method of operation of a cochlear implant system. The method can include implanting a cochlear electrode, a stimulator, and a battery into a person and further implanting a first near field communication interface proximate an ear canal of the person. The stimulator can be in electrical communication with the cochlear electrode and the first near field communication interface. The battery can be in electrical communication with the first near field communication interface. The method can further include inserting a removable earplug into the ear canal. The removable earplug can include a sensor, a signal processor, and a second near field communication interface with the signal processor in electrical communication with the sensor and the second near field communication interface. Inserting the removable earplug into the ear canal can be performed such that the second near field communication interface is aligned with the first near field communication interface. The aligned communication interfaces can provide electrical power to the removable earplug from the battery via the first near field communication interface and the second near field communication interface.

DETAILED DESCRIPTION

Figure 1:
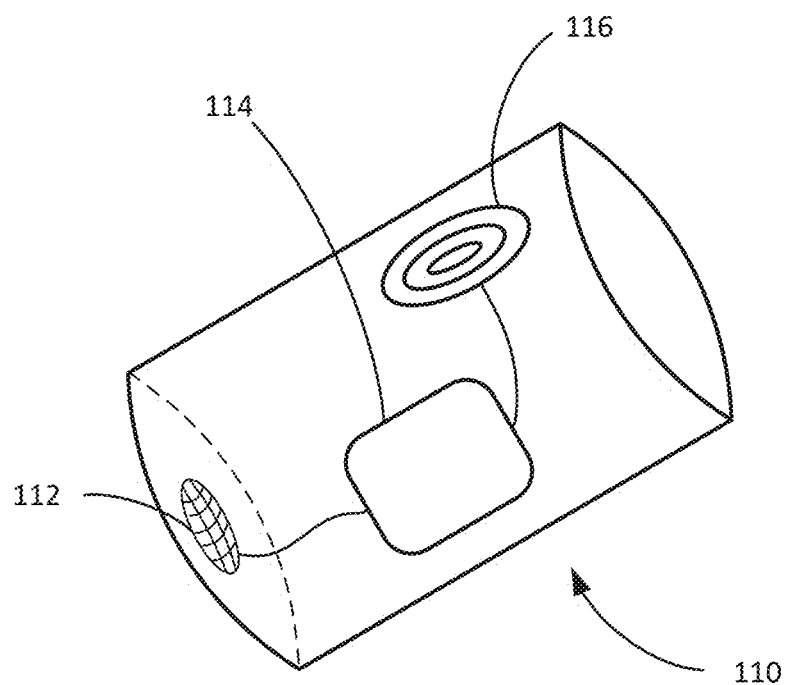
FIG. 1 illustrates a schematic of an example removable earplug according to an aspect of the present disclosure.

Aspects of this disclosure describe implantable cochlear implant systems including a removable earplug sensor. FIG. 1 illustrates a schematic of an example removable earplug according to an aspect of the present disclosure. The removable earplug 110 of FIG. 1 includes a sensor 112 configured to sense auditory signals and generate input signals representative of the sensed auditory signals. The sensor 112 of the removable earplug 110 can be any type of sensor which can sense auditory signals. For example, in some embodiments, the sensor 112 is a microphone which can sense auditory signals and can generate an input signal representative of the sensed auditory signals.

The removable earplug 110 of FIG. 1 further includes a signal processor 114 which is in electrical communication with the sensor 112 and is configured to receive input signals from the sensor 112 and generate a stimulation signal based on the received input signal. The signal processor 114 can be any type of processor and in some embodiments, the signal processor 114 can comprise a digital signal processor, one or more microprocessors, microcontrollers, application specific integrated circuits (ASICs) or other types of processors. Supporting circuitry for one or more such components can also be included as a part of the signal processor 114. In some embodiments, the signal processor 114 can include or otherwise communicate with a memory containing programming for operating one or more components.

In some embodiments, the output of the signal processor can be based on a lookup table or other programmed (e.g., in memory) correspondence between the received signal from the sensor and the stimulation signal output from the signal processor 114. While not necessarily based explicitly on a function, the relationship between the input to the signal processor (e.g., from the internal sensor such as a microphone) and the output of the signal processor (e.g., via near field communication interface) is referred to as the transfer function of the signal processor.

The removable earplug 110 also includes a near field communication interface 116 in electrical communication with the signal processor 114. In some embodiments, the near field communication interface 116 comprises one or more coils of wire. For example, the near field communication interface 116 can be a coil of copper wire. In some examples, such a coil is included within a biocompatible housing. In other examples, a coil can be made from a biocompatible material. In operation, the near field communication interface 116 can communicate electrical signals (e.g., stimulation signals) and/or electrical power to and/or from the removable earplug 110 to another device, such as a device including a corresponding near field communication interface. In some such embodiments, near field communication interface 116 is configured to communicate with a corresponding near field communication interface if the near field communication interfaces are positioned closely enough together and aligned properly to facilitate near field communication (e.g., inductive communication between corresponding coils).

Figure 2A:
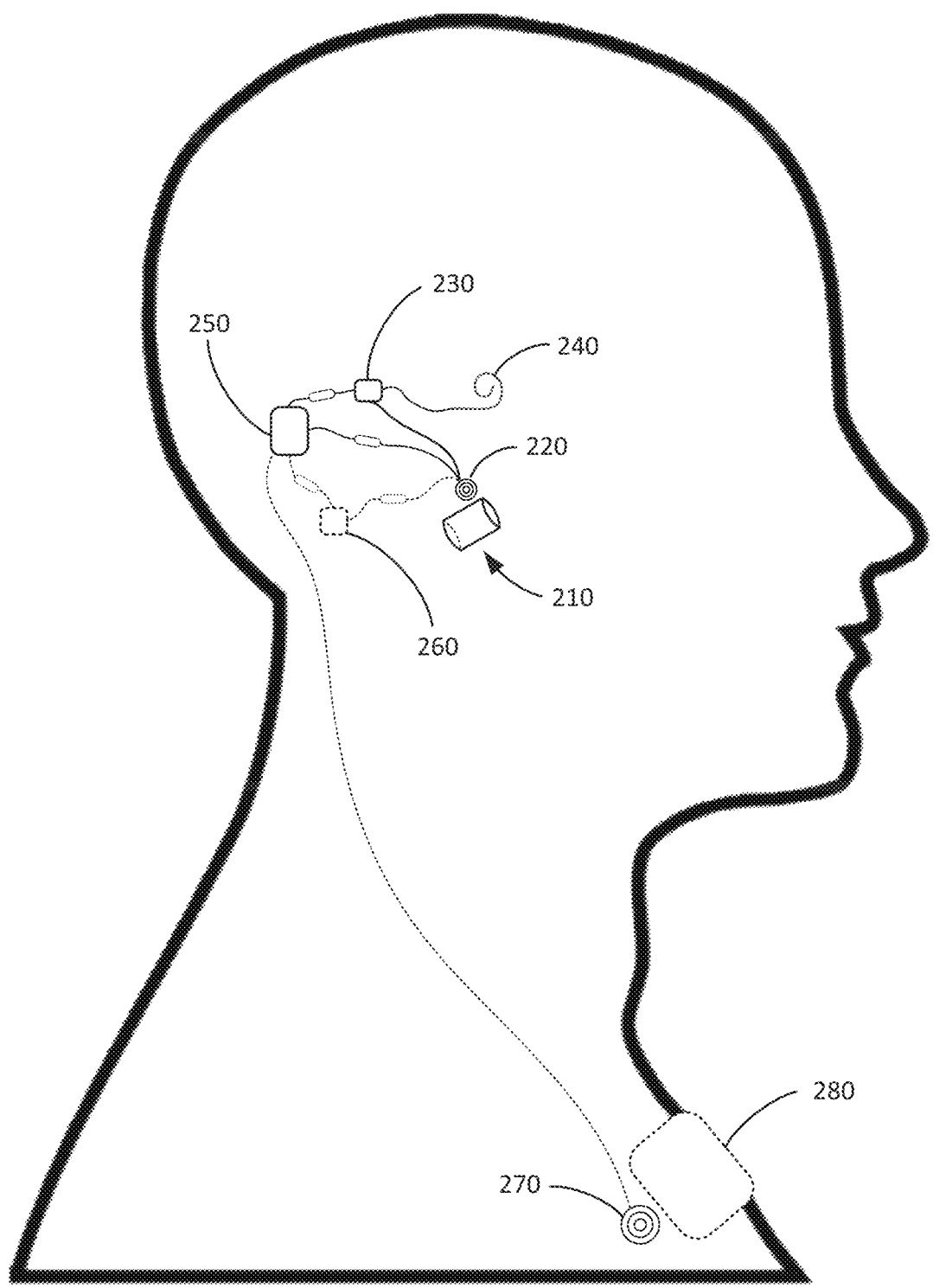
FIG. 2A illustrates a schematic of one embodiment of a cochlear implant system with a removable earplug according to an aspect of the present disclosure.

FIG. 2A illustrates a schematic of one embodiment of a cochlear implant system with a removable earplug according to an aspect of the present disclosure. The system of FIG. 2A includes a removable earplug 210 configured to communicate with system components via a near field communication interface 220. In some embodiments, the near field communication interface 220 is implanted subcutaneously proximate a wearer's ear canal. In some such embodiments, the removable earplug 210 is configured to be inserted into an ear canal such that a corresponding near field communication interface of the ear plug, such as 116 in FIG. 1, can communicate with implanted near field communication interface 220. For clarity, the implanted near field communication interface 220 is referred to as a first near field communication interface and a corresponding near field communication interface in the removable earplug 210 is referred to as a second near field communication interface.

In some examples, the removable earplug 210 is configured to be inserted into an ear canal of a patient when in use. As described with respect to FIG. 1, in some embodiments, the removable earplug 210 can be configured to detect incoming auditory signals (e.g. sound waves) with a sensor, process the auditory signals via a signal processor (e.g., signal processor 114), and generate output signals (e.g., stimulation signals) representative of the detected auditory signals. The removable earplug 210 can further provide the generated output signal to the implanted system via first and second near field communication interfaces.

The system of FIG. 2A further includes a cochlear electrode 240 implanted into the cochlear tissues of a patient. The cochlear electrode 240 is in electrical communication with the stimulator 230, which can be configured to provide electrical stimulus signals to the cochlear electrode 240 in response to input signals (e.g. stimulation signals) received by the stimulator 230. In some examples, the cochlear electrode 240 is fixedly attached to the stimulator 230. In other examples, the cochlear electrode 240 is removably attached to the stimulator 230. As shown, the stimulator 230 is in communication with the near field communication interface 220. In some embodiments, the stimulator 230 provides electrical signals to the cochlear electrode 240 based on stimulation signals from the removable earplug 210 through the near field communication interface 220.

In various embodiments, the cochlear electrode 240 can include any number of contact electrodes in electrical contact with different parts of a patient's cochlear tissue, for example, as described in PCT patent application No. PCT/US20/19166, which is incorporated by reference. In such embodiments, the stimulator 230 can be configured to provide electrical signals to any number of such contact electrodes to stimulate the cochlear tissue. For example, in some embodiments, the stimulator 230 is configured to activate different contact electrodes or combinations of contact electrodes of the cochlear electrode 240 in response to different stimulation signals received from the removable earplug 210. This can help the patient differentiate between different input signals. In some embodiments, more than one cochlear electrode is included in the cochlear implant system.

The system of FIG. 2A also includes an implantable battery 250 in electrical communication with the near field communication interface 220 and the stimulator 230. The battery can be any type of battery and in some examples, the battery 250 can be a rechargeable battery. For example, in some embodiments, the battery 250 is an implantable, rechargeable, lithium-ion battery. Further, the battery 250 can have any capacity, but, in some embodiments, the battery 250 has a capacity of at least 3 Watt-hours, at least 3.5 Watt-hours, or at least 4 Watt-hours. In some embodiments, the battery 250 has a capacity of approximately 3.7 Watt-hours. In some embodiments, battery 250 has a capacity of approximately 100 milliamp hours. For instance, in some such examples, battery 250 comprises a 3.7 volt lithium-ion battery having a capacity of 100 milliamp hours. While example systems described herein are described using a battery, it will be appreciated that other rechargeable energy storage device known to those skilled in the art can be used. Example rechargeable energy storage devices include batteries and capacitors, such supercapacitors.

The battery 250 can be a rechargeable battery or other energy storage technology and can provide power to the various components of the cochlear implant system. For example, as described, the battery 250 can provide power to the near field communication interface 220 and the stimulator 230. In some examples, battery 250 provides electrical power to the stimulator such that the stimulator can provide electrical stimuli via the cochlear electrode 240.

In some examples, the battery 250 can be implanted in the pectoral region of the patient in order to provide adequate room for larger equipment (e.g. a relatively large battery) for prolonged operation (e.g. longer battery life). Additionally, in the event a battery needs eventual replacement, a replacement procedure in the patient's pectoral region can be performed several times without certain vascularization issues that can arise near the location of the cochlear implant. For example, in some cases, repeated procedures (e.g., battery replacement) near the cochlear implant can result in a decreased ability for the skin in the region to heal after a procedure. Placing a replaceable component such as a battery in the pectoral region can facilitate replacement procedures with reduced risk for such issues.

In some embodiments, the battery 250 is configured to be implanted in the head of a person as in FIG. 2A. Such placement of the battery 250 can facilitate easier incorporation of the battery 250 into the overall system because it is implanted closer to the other components of the cochlear implant system. Further, such a placement decreases the length of connections between the battery and the components of the cochlear implant system to which it provides power. Shorter connections between the battery and the components it powers can decrease the power lost in transmission from the battery to the components.

The battery 250 can also be in electrical communication with a charging coil 270 which can be implanted in the patient. The charging coil 270 can enable the battery to be recharged and can be made of one or more coils of wire of conductive material such as copper. In some examples, such a coil is included within a biocompatible housing. In other examples, such a coil is made from a biocompatible material. In some examples, the charging coil 270 can communicate electrically with an external device (shown here as external device 280) which is external to the patient. The external device 280 can be an external charging device which is configured to transmit power. The external device 280 can also include one or more coils of wire made of conductive material and capable of communicating with and providing power to the charging coil 270 of the system through the skin of the wearer. In the embodiment of FIG. 2A, the charging coil 270 is in wireless communication with the external device 280. The charging coil 270 can be in wireless communication with the external device 280, such as via an inductive communication, whereby electrical energy can be transferred from the one or more coils of the external device 280 to the charging coil 270.

For example, in operation, the charging coil 270 can be configured to receive electrical energy from the external device 280 wirelessly via induction. The charging coil 270 can transmit electrical energy received from the external device 280 through one or more leads into the battery 250 in the form of electrical charge. Thus, the external device 280 can be configured to wirelessly provide electrical power to the charging coil 270 to recharge the battery 250.

In the embodiment of FIG. 2A, the charging coil 270 is implanted in a pectoral region of the human being, however, the charging coil 270 coil can be implanted anywhere within the patient. Implanting the charging coil 270 into a region such as the pectoral region of a patient can be advantageous as such placement can facilitate placement of the external device 280 in a position where the external device 280 can more easily transmit power wirelessly into the charging coil 270. However, in some examples, charging coil 270 can be implanted in the head or other body part of the wearer.

Continuing with the embodiment of FIG. 2A, the battery 250 can provide power to the near field communication interface 220. The near field communication interface 220 can further transmit the power received from the battery 250 into the removable earplug 210, for example, when near field communication interface 220 and a corresponding near field communication interface (e.g., 116) of the removable earplug 210 are aligned. In some embodiments, the near field communication interface 220 transmits the power received from the battery 250 wirelessly into the removable earplug 210. In some embodiments, the near field communication interface 220 is made of one or more coils of wire such as copper. In some examples, such a coil is included within a biocompatible housing. In other examples, such a coil is made from a biocompatible material. In some embodiments, the near field communication interface 220 can transmit power wirelessly via induction. For example, in some embodiments, the near field communication interface of the removable earplug 210 is made of one or more coils of wire (e.g. copper) configured to interface with the one or more coils of wire of the near field communication interface 220 via induction. In such embodiments, power can be transmitted from the battery 250 into the removable earplug 210 through the coils of the near field communication interface and the removable earplug 210.

In some embodiments, the near field communication interface 220 is a first near field communication interface while the near field communication interface of the removable earplug 210 (e.g., near field communication interface 116 in FIG. 1) is a second near field communication interface.

In FIG. 2A, the near field communication interface 220 is implanted subcutaneously in the patient. In some embodiments, the near field communication interface 220 can be configured to be implanted subcutaneously proximate an ear canal. Implanting the near field communication interface 220 proximate the ear canal of the patient, allows convenient wireless transmission of power from the battery 250 into the removable earplug 210 when the removable earplug is inserted into the ear canal. For example, when the removable earplug 210 is inserted into the ear canal of the patient, the first near field communication interface (e.g. 220) and the second near field communication interface (e.g. of the removable earplug) can be positioned proximate each other. Such a proximate position allows for efficient transmission of power from the first near field communication interface to the second near field communication interface.

As the battery 250 can provide power to the removable earplug 210. It can be advantageous to include an implanted power source separately from the removable earplug. For example, a power source within a removable earplug requires space within the removable earplug, and will be size-limited if the removable earplug is to fit within an ear canal. A removable earplug with a small integrated power source, for example, to facilitate insertion into an ear canal, may require frequent recharging and/or replacement because of limited energy capacity in the power source contained within the earplug.

Since the battery 250 is external to the removable earplug, the battery 250 can be larger than a battery configured to fit within the removable earplug while allowing the removable earplug to fit within an ear canal of a wearer. Thus, in some cases, an implanted battery (e.g., 250) can power components within the removable earplug (e.g., via near field communication interface 222) for a longer period of time than a small battery within the earplug itself. In such cases, a user does not need to recharge or replace earplugs due to limited battery capacity of the earplug itself. An implanted battery 250 powering components of the removable earplug can increase the duration of operation of the system before a recharge is required compared to systems in which components of the earplug are powered by a battery within the earplug itself. In some embodiments, the removable earplug 210 does not include an internal power source and components thereof are powered via the implanted battery 250 and near field communication interface 222.

In some embodiments, the battery 250 does not output electrical energy until the first near field communication interface and the second near field communication interface are in wireless communication with each other. For example, in some embodiments, the battery 250 does not output electrical energy when the removable earplug 210 is not inserted into the ear canal of a patient. However, once the removable earplug 210, including the second near field communication interface, is inserted into the ear canal of the patient and the first near field communication interface 220 is in wireless communication with the second near field communication interface, the battery 250 can provide power to the removable earplug 210. Such configurations can be advantageous because the battery 250 does not unnecessarily use power when the removable earplug 210 is not inserted. This can prolong the time before the battery 250 needs to be recharged.

In some examples, battery 250 provides electrical power to the stimulator 230 even when the removable earplug is not inserted into the ear canal. However, in some such examples, if the removable earplug 210 is not inserted into the ear canal, the stimulator does not receive any stimulation signals from the removable earplug 210 and therefore does not draw much power from the battery 250.

In some embodiments, during operation, the removable earplug 210 includes a sensor (e.g., 112), a signal processor (e.g., 114) and a second near field communication interface (e.g., 116). The removable earplug 210 is configured to receive power from battery 250 and first near field communication interface 220 via second near field communication interface (e.g., 116), which can be used to provide electrical power to the sensor and signal processor.

The sensor can be configured to receive acoustic stimuli and provide input signals to a signal processor, which and generate stimulation signals based on the received input signals. The signal processor can output stimulation signals to the second near field communication interface, which can communicate the stimulation signals to stimulator 230 via first near field communication interface 220.

Thus, in some embodiments, an implanted first near field communication interface 220 and a second near field communication interface (e.g., 116) included in the removable earplug can be used to provide electrical power from an implanted battery 250 to components within the removable earplug 210. Such communication can also provide data (e.g., stimulation signals) from the removable earplug 210 to an implanted stimulator.

In some embodiments, the cochlear implant system includes an implanted signal processor 260. In various examples, the signal processor 260 can comprise any variety of components, for example, digital and/or analog processing components. In some embodiments, signal processor 260 comprises a digital signal processor, one or more microprocessors, microcontrollers, application specific integrated circuits (ASICs) or the like. Supporting circuitry for one or more such components can also be included as a part of the signal processor 260. In some embodiments, the signal processor 260 can include or otherwise communicate with a memory containing programming for operating one or more components. Implanted signal processor 260 can receive electrical power from battery 250.

In some such embodiments, the signal processor 260 can replace the processing performed by the signal processor of the removable earplug. For example, the signal processor 260 can receive an input signal representative of auditory signals from the removable earplug 210 (e.g., via first and second near field communication interfaces) and generate stimulation signal based on the received input signal representative of the auditory signals. However, in some embodiments, the signal processor 260 is an additional processor which can receive signals from the removable earplug 210 and perform additional processing on the received signals.

For example, the signal processor 260 can be programmed with instructions to receive a stimulation signal from removable earplug 210 and output a modified stimulation signal. In some embodiments, the output of the signal processor 260 can be calculated using an equation based on received signals. Alternatively, in some embodiments, the output of the signal processor 260 can be based on a lookup table or other programmed (e.g., in memory) correspondence between the received signal from the removable earplug 210 and the output signal. While not necessarily based explicitly on a function, the relationship between the input to the signal processor 260 (e.g., from the removable earplug 210) and the output of the signal processor 260 is referred to as the transfer function of the signal processor 260. In some embodiments, the signal processor of the removable earplug 210 comprises a first signal processor and the implanted signal processor 260 comprises a second signal processor. In some embodiments, the first and second signal processors operate together according to an overall transfer function that describes the relationship between an input signal received by the first signal processor and the modified stimulation signal output from the second signal processor.

During one exemplary operation of the cochlear implant system which includes the implanted signal processor 260, the removable earplug 210 detects audio signals. The signal processor 260 can receive input signals from the removable earplug 210 via first and second near field communication interfaces and generate stimulation signals based on the received input signals based on the transfer function of the signal processor 260. The signal processor 260 can output stimulation signals to the stimulator 230, which can then provide electrical stimuli via one or more contact electrodes of the cochlear electrode 240 based on the received stimulation signals from the signal processor 260.

During another example embodiment, a signal processor of the removable earplug is configured to generate stimulation signals as described elsewhere herein and communicate such stimulation signals to the implanted system via near field communication interfaces. The implanted signal processor 260 can be configured to receive the stimulation signals and output modified stimulation signals to the stimulator 230. In some embodiments, a signal processor within a removable earplug is programmed with a standard transfer function independent of the user while the implanted signal processor 260 can be customized to fit the wearer (e.g., based on the needs of the wearer).

Figure 2B:
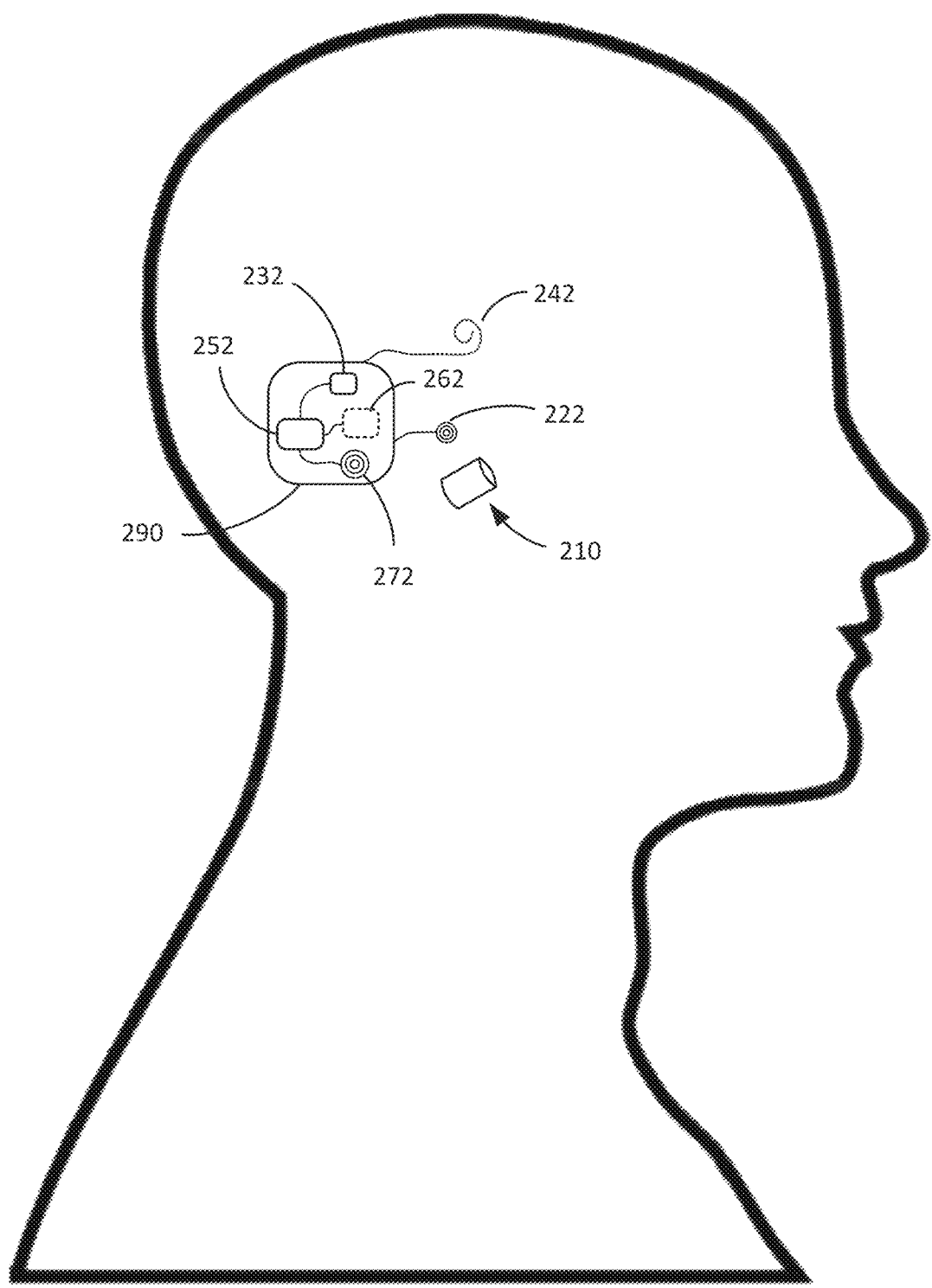
FIG. 2B illustrates a schematic of another embodiment of a cochlear implant system with a removable earplug according to an aspect of the present disclosure.

While implanted components are generally shown as being discretely implanted components, in some embodiments, one or more such components can be housed within a single housing. FIG. 2B illustrates a schematic of another embodiment of a cochlear implant system with a removable earplug 210 according to an aspect of the present disclosure.

The cochlear implant system includes a removable earplug 210 (e.g., removable earplug 110 in FIG. 1) in communication with a near field communication interface 222 (e.g., via a corresponding near field communication interface in removable earplug 210). The system also includes a stimulator 232, a cochlear electrode 242, a battery 252, a charging coil 272, and a housing 290. In some embodiments, housing 290 further includes an implanted signal processor 262.

During example operation, the removable earplug 210 can receive audio signals, process the audio signals, and can generate and send stimulation signals to the stimulator 232 through the near field communication interface 222. The stimulator 232 can output electrical stimuli corresponding to the received stimulation signals from the removable earplug 210 to the cochlear electrode 242 in order to stimulate a patient's cochlear tissue. In some embodiments, the optional implanted signal processor 262 processes signals from the removable earplug 210 and generates and sends stimulation signals or modified stimulation signals to the stimulator 232 such as described with respect to FIG. 2A.

In comparison to the embodiment of FIG. 2A, however, the system of FIG. 2B includes a housing 290 which houses many components of the cochlear implant system. In some embodiments, the housing 290 includes the stimulator 232, the battery 252, the charging coil 272, and optionally, the implanted signal processor 262. However, in various examples the housing 290 does not need to include all the listed elements. For example, in some embodiments, the battery 252 and the charging coil 272 are housed in the housing 290. In some examples, the stimulator 232 is housed in the housing 290 along with the battery 252 and the charging coil 272. Including such elements into a housing can facilitate implantation of the system in a wearer.

Further, while shown as being outside of the housing 290 in FIG. 2B, in some embodiments, the near field communication interface 222 is included within housing 290. In other embodiments, the near field communication interface 222 is not included in the housing 290 as shown in FIG. 2B. In some such embodiments, it can be easier to implant the near field communication interface 222 proximate the ear canal of a wearer to facilitate communicate with removable earplug 210 when the near field communication interface is outside of housing 290. Additionally, implanting the near field communication interface 222 outside the housing 290 can allow the housing 290 to be positioned in a location further away from a patient's ear canal which can decrease possible scar tissue development in the area. In general, near field communication interface 222 can be included within the housing 290 or outside of the housing 290. In embodiments in which the near field communication interface 222 is outside of the housing 290, the near field communication interface 222 can comprise a coil contained within a separate biocompatible housing or a biocompatible coil not contained within a housing such as described elsewhere herein.

Additionally or alternatively, in some examples, charging coil 272 can be positioned outside of the housing. In some examples, the charging coil 272 can be positioned in a location to allow ease of external charger placement, such as in a pectoral region (as shown in the example of FIG. 2A). Charging coil can be included in a separate biocompatible housing or made from a biocompatible material.

The housing 290 can take any shape and size and can further be made of any material. In some embodiments, the housing 290 is a hermetically sealed housing comprising biocompatible materials. The housing 290 can include feedthroughs providing communication from external components to the internal components enclosed in the housing 290. Feedthroughs can provide electrical communication between the internal and external components of the housing 290 via leads extending from the housing 290 and/or connectors integrated into the components outside the housing.

In the illustrated examples of FIG. 2A and FIG. 2B, the connections between various implanted elements can include a plurality of isolated conductors providing a plurality of communication channels between various components of the system. The connections can include a coating such as an electrically insulating sheath to minimize any conduction of electrical signals to the body of the patient. In various embodiments, one or more communication leads can be detachable such that communication between two components can be disconnected in order to electrically and/or mechanically separate such components. For instance, in some embodiments, a lead can include a detachable connector. A detachable connector can facilitate decoupling of the various components of the implant portion of the cochlear implant system. Example detachable connectors are described in PCT patent application No. PCT/US20/19166, which is incorporated by reference.

Figure 3A:
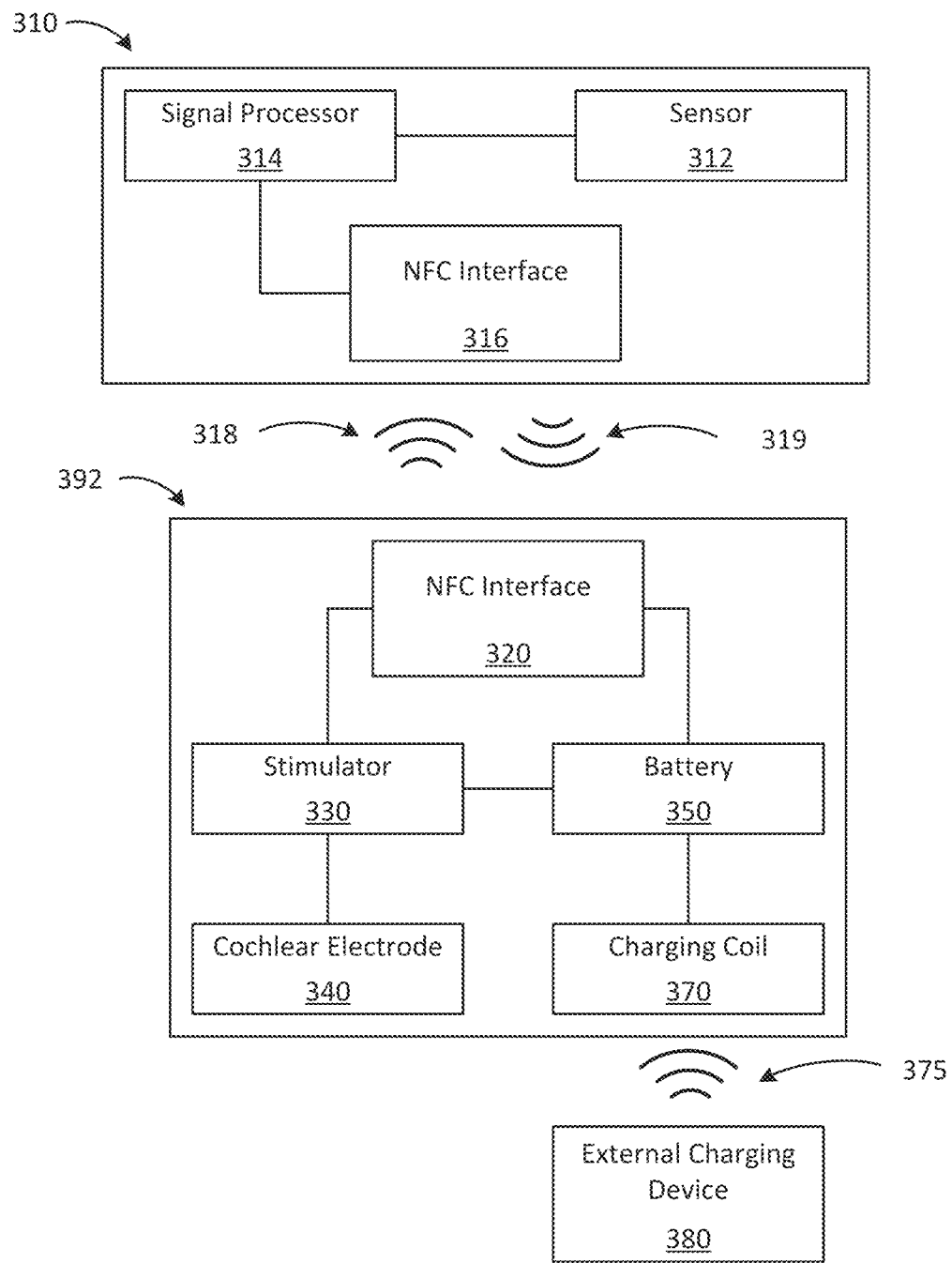
FIG. 3A illustrates a block diagram of an exemplary cochlear implant system including a removable earplug according to an aspect of the present disclosure.

FIG. 3A illustrates a block diagram of an example cochlear implant system including a removable earplug. The cochlear implant system of FIG. 3A includes a removable earplug 310, an implantable subsystem 392, and an external charging device 380. In the illustrated example, the removable earplug 310 is in wireless communication with the implantable subsystem 392 via the near field communication (NFC) interfaces 316, 320. In some embodiments, the near field communication interface 320 of the implantable subsystem is a first near field communication interface and the near field communication interface 316 of the removable earplug 310 is a second near field communication interface. The implantable subsystem 392 can also be in wireless communication with the external charging device via a charging coil 370.

The removable earplug 310 of FIG. 3A comprises a sensor 312 in communication with a signal processor 314 which is in further communication with the near field communication interface 316. The implantable subsystem 392 of FIG. 3A comprises a near field communication interface 320 in electrical communication with a stimulator which is in further communication with a cochlear electrode 340. The implantable subsystem 392 also comprises a battery 350 which is in electrical communication with the near field communication interface 320, the stimulator 330, and the charging coil 370.

In an example operation of the embodiment of FIG. 3A, the sensor 312 senses auditory signals and generates an input signal representative of the sensed auditory signals. The signal processor 314 can receive the input signal from the sensor 312 and generate a stimulation signal based on the received input signal. Further, when the removable earplug 310 is inserted into a patient's ear canal, the first near field communication interface 320 and the second near field communication interface 316 are positioned proximate each other. The proximate position can establish a communication link between the first near field communication interface 320 and the second near field communication interface 316. The signal processor 314 can communicate the generated stimulation signal to the stimulator 330 in the implantable subsystem 392 via the communication link as shown by 319.

Additionally, in the illustrated example, the battery 350 of the implantable subsystem 392 provides electrical power to the removable earplug 310 via the communication link as shown by 318. In some embodiments, power received at the removable earplug 310 via the communication link powers the sensor 312 and/or the signal processor 314 during operation. Thus, in some embodiments, one or more of the steps of sensing an auditory signal, generating an input signal representative thereof, and generating a stimulation signal based on the input signal are only performed once the removable earplug 310 is inserted into an ear canal proximate the near field communication interface 320 of the implantable subsystem 392 such that the sensor 312 and/or signal processor 314 are powered via battery 350 and the established communication link.

As shown, the charging coil 370, which is in electrical communication with the battery 350, can wirelessly receive electrical energy from the external charging device 380, as shown by 375, and can provide electrical charge to the battery 350 to recharge the battery 350.

In some embodiments, when the removable earplug 310 is inserted into a patient's ear canal such that the near field communication interface 316 and the implanted near field communication interface 320 are aligned, the battery provides power to the removable earplug through the aligned communication interfaces. Additionally or alternatively, when the removable earplug 310 is inserted into a patient's ear canal such that the near field communication interface 316 and the implanted near field communication interface 320 are aligned, the signal processor 314 of the removable earplug 310 outputs a stimulation signal to the stimulator through the aligned near field communication interfaces.

Figure 3B:
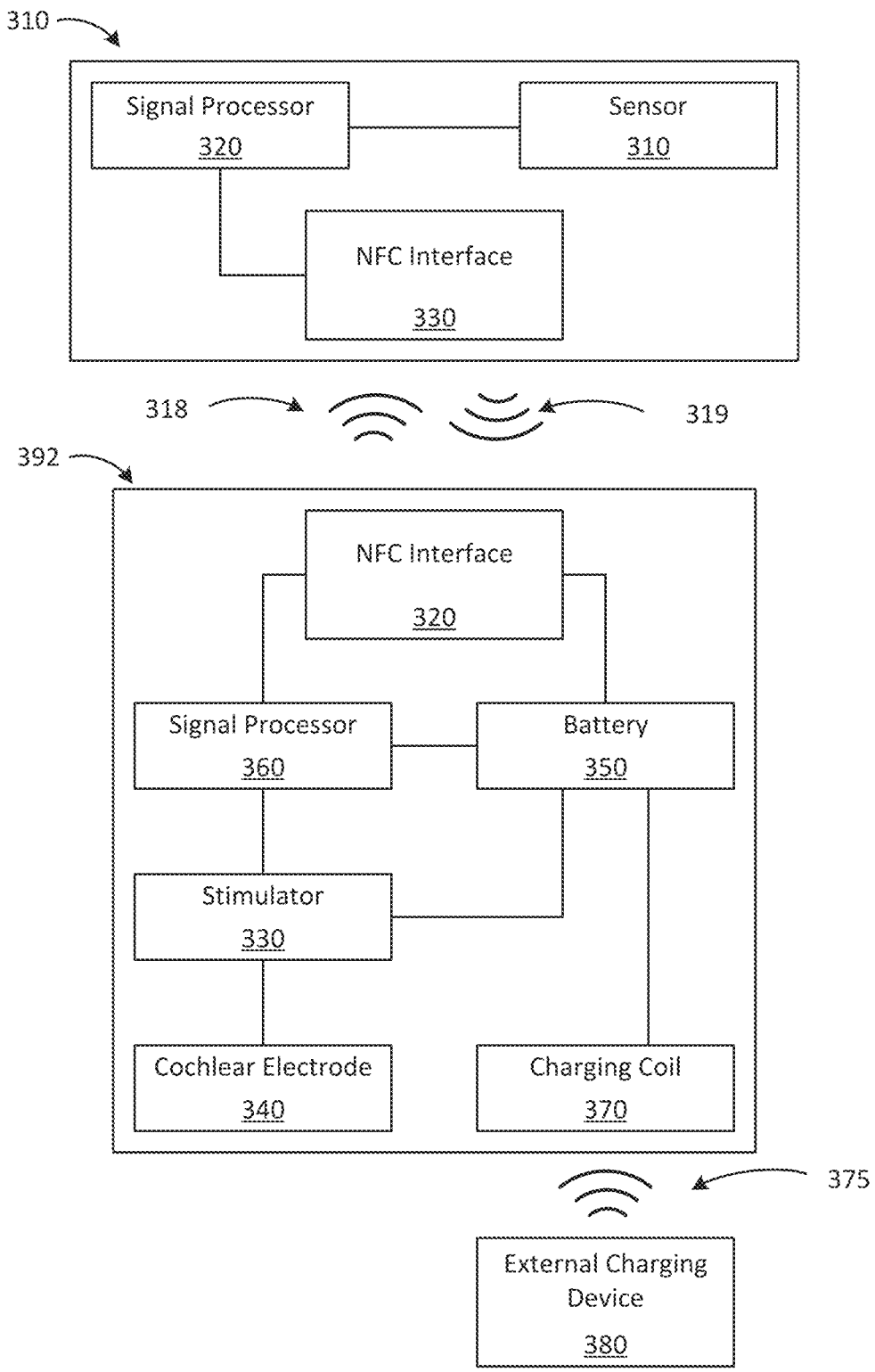
FIG. 3B illustrates a block diagram of another exemplary cochlear implant system including a removable earplug according to an aspect of the present disclosure.

Moving to FIG. 3B, FIG. 3B illustrates a block diagram of another exemplary cochlear implant system including a removable earplug 310 according to an aspect of the present disclosure. In contrast to the embodiment of FIG. 3A, the implantable subsystem 392 of FIG. 3B includes an implanted signal processor 360. In the embodiment of FIG. 3B, the implanted signal processor 360 is in electrical communication with the near field communication interface 320 and the stimulator 330. Further, the implanted signal processor 360 can receive power through its electrical communication with the battery 350.

In the embodiment of FIG. 3B, the signal processor of the removable earplug 310 comprises a signal processor 314 and the implantable subsystem comprises an implanted signal processor 360. The implanted signal processor 360 is in electrical communication with the first near field communication interface 320 and can be programmed with a transfer function. Further, the implanted signal processor 360 can be configured to receive the stimulation signal from the signal processor 314 when the first near field communication interface 320 and the second near field communication interface are in wireless communication with each other. Additionally, in some embodiments, the implanted signal processor 360 can be configured to output a modified stimulation signal to the stimulator 330 based on the received stimulation signal and the transfer function.

Figure 4:
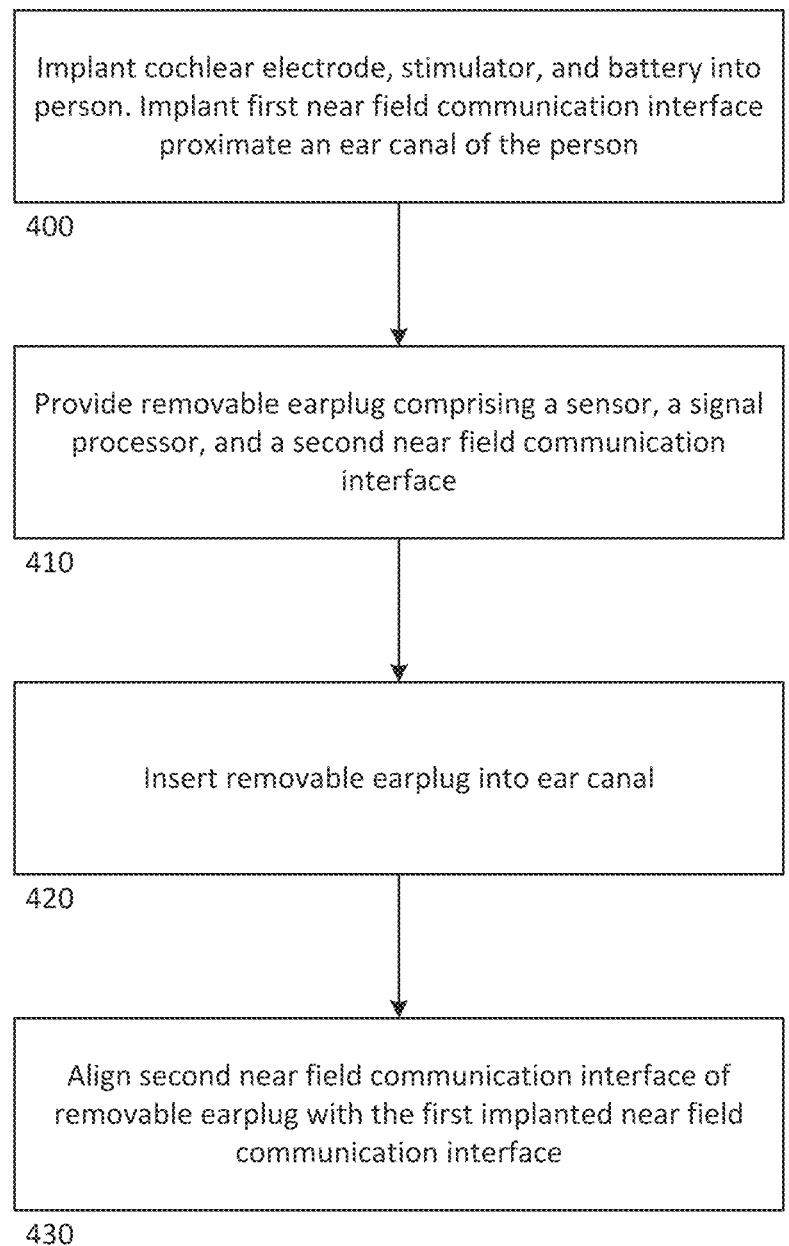
FIG. 4 is a flow diagram of an example method of operating a cochlear implant system according to an aspect of the present disclosure.

FIG. 4 is a flow diagram of an example method of operating a cochlear implant system according to an aspect of the present disclosure. Starting at 400, the method includes implanting a cochlear electrode, a stimulator, and a battery into a person. Further, the method includes implanting a first near field communication interface proximate an ear canal of the person. When implanted, the stimulator is in electrical communication with the cochlear electrode and the first near field communication interface. Additionally, when implanted, the battery is in electrical communication with the first near field communication interface and stimulator. The method continues in step 410 with providing a removable earplug comprising a sensor, a signal processor, and a second near field communication interface. The signal processor can be in electrical communication with the sensor and the second near field communication interface. In some embodiments, the sensor can be configured to detect auditory signals and generate an input signal which is received by the signal processor. In some such embodiments, the signal processor can be configured to receive the input signal from the sensor and transform the input signal into a stimulation signal by applying a transfer function to the input signal. Further, in step 420, the method includes inserting the removable earplug into the person's ear canal. The method also includes in step 430 aligning the second near field communication interface with the first near field communication interface. In some embodiments, aligning the second near field communication interface with the first near field communication interface is performed as part of the insertion of the removable earplug into a person's ear canal. When the second near field communication interface is aligned with the first near field communication interface, the battery can provide electrical power to the removable earplug via the first near field communication interface and the second near field communication interface. Similarly, when the second near field communication interface is aligned with the first near field communication interface, the stimulator can receive stimulation signals from the signal processor of the ear plug via the first and second near field communication interfaces.

In some embodiments, a wearer is alerted when the first and second near field communication interfaces are aligned. For example, in some embodiments, an implanted stimulator does not receive any stimulation signals and does not provide any electrical stimuli to a wearer's tissue when the near field communication interfaces are not aligned and communication is not enabled. However, in some such embodiments, once the first and second near field communication interfaces are aligned, the removable earplug receives power via the near field communication interfaces and provides a stimulation signal to the implanted stimulator. The stimulator can, in response thereto, apply electrical stimuli via the cochlear electrode. Accordingly, in some embodiments, the wearer can "hear" when the first and second near field communication interfaces are aligned based on the detected onset of stimulation via the stimulator.

Figure 5:
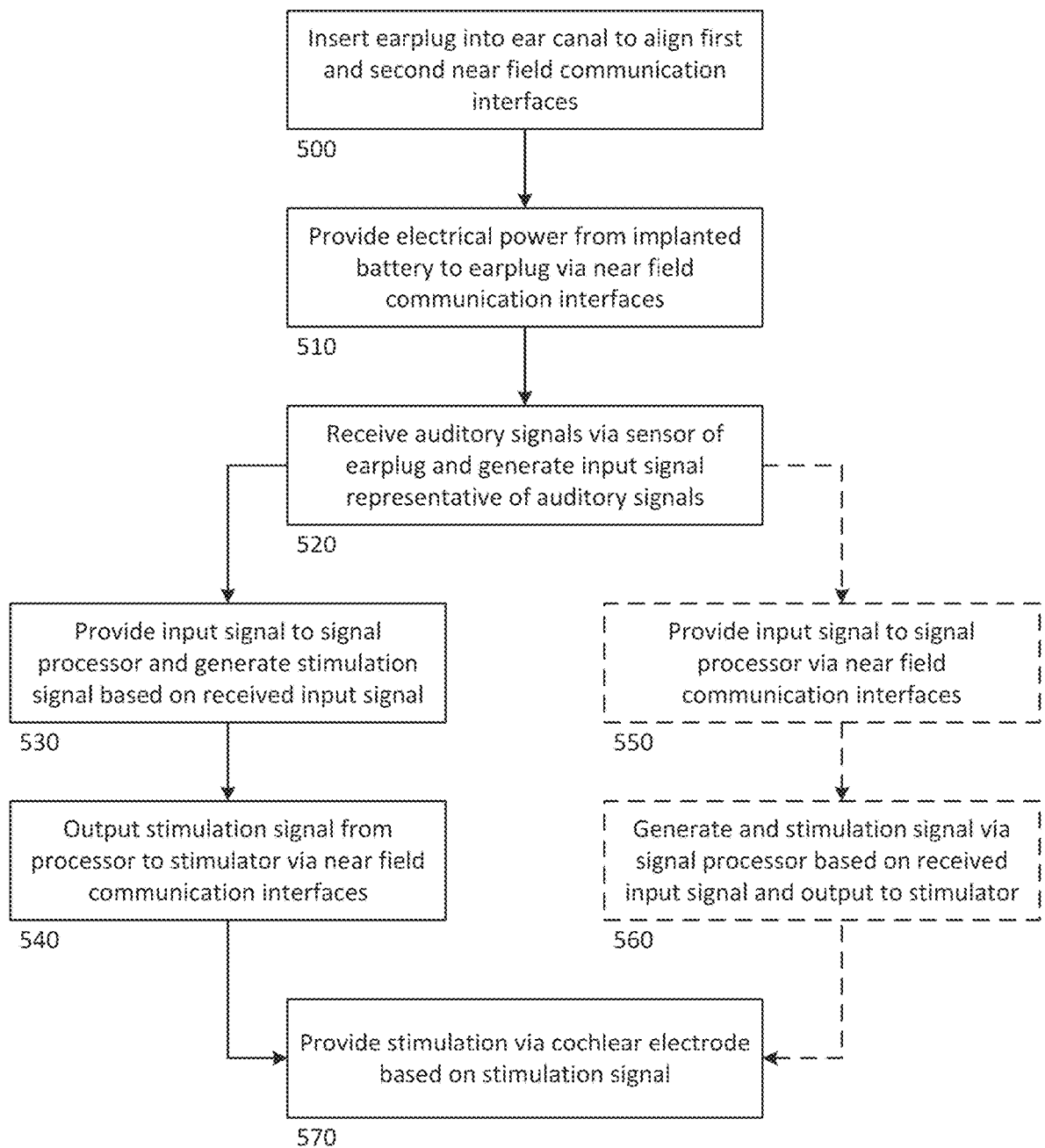
FIG. 5 is a flow diagram of another example method of operating a cochlear implant system according to an aspect of the present disclosure.

FIG. 5 is a flow diagram of another example method of operating a cochlear implant system according to some embodiments of the present disclosure. At 500, the method includes inserting a removable earplug into a person's ear canal to align a first and second near field communication interface. At 510, the method includes providing electrical power from an implanted battery to the removable earplug via the near field communication interfaces. At 520, the method includes receiving auditory signals via a sensor of the removable earplug and generating an input signal representative of the auditory signals. The method can then continue with step 530 or 550 depending on if an optional implanted signal processor is included in the cochlear implant system.

In the cases in which no implanted signal processor is present, the method continues with step 530. At 530, the method includes providing the input signal to the signal processor of the removable earplug and generating a stimulation signal based on the received input signal. Next, at step 540, the method includes outputting the stimulation signal from the signal processor to the stimulator via the near field communication interfaces. At step 570, the method includes providing stimulation via an implanted cochlear electrode based on the stimulation signal. While described with respect to embodiments in which to implanted signal processor is present, it will be appreciated that such steps may be performed in embodiments in which an implanted signal processor is present, for example, in embodiments in which an implanted signal processor is not involved in generating stimulation signals based on input signals from the removable ear plug.

In some embodiments in which an implanted signal processor is present, the method can move to step 550 from step 520. At step 550, the method includes providing the input signal to the implanted signal processor via the near field communication interfaces. Next, at step 560, the method includes generating a stimulation signal via the signal processor based on the received input signal and outputting the stimulation signal to a stimulator. Again, at step 570, the method includes providing stimulation via the implanted cochlear electrode based on the stimulation signal. As the implanted signal processor can be in communication with the stimulator, the stimulation signal does not need to be communicated via near field communication interfaces.

While not shown in FIG. 5, as described elsewhere herein, in some examples, a signal processor in a removable earplug can be used in combination with an implantable signal processor. For example, an input signal can be sent to a signal processor within the removable earplug, which can generate a stimulation signal as in step 530. The stimulation signal can be output via near field communication interfaces to an implanted signal processor, which can receive the stimulation signal and generate a modified stimulation signal as described herein. The modified stimulation signal can be provided to a stimulator, which can provide stimulation via a cochlear electrode based on the received modified stimulation signal.

While often described herein as using an electrical stimulator to stimulate the patient's cochlear tissue via a cochlear electrode, in some examples, the system can additionally or alternatively include an acoustic stimulator. An acoustic stimulator can include, for example, a transducer (e.g., a piezoelectric transducer) configured to provide mechanical stimulation to the patient's ear structure. In an exemplary embodiment, the acoustic stimulator can be configured to stimulate one or more portions of the patient's ossicular chain via amplified vibrations. Acoustic stimulators can include any appropriate acoustic stimulators, such as those found in the ESTEEM™ implant (Envoy Medical Corp., St. Paul, Minn.) or as described in U.S. Pat. Nos. 4,729,366, 4,850,962, and 7,524,278, and U.S. Patent Publication No. 20100042183, each of which is incorporated herein by reference in its entirety.

Various non-limiting embodiments have been described. These and others are within the scope of the following claims.

The invention claimed is:

1. A cochlear implant system comprising:
an implantable subsystem comprising:
a cochlear electrode;
a stimulator in electrical communication with the cochlear electrode;
a rechargeable energy storage device in electrical communication with the stimulator;
a first near field communication interface in electrical communication with the rechargeable energy storage device and configured to be implanted subcutaneously proximate an ear canal; and
a removable earplug configured to be inserted into the ear canal and comprising:
a sensor configured to sense auditory signals and generate an input signal representative of the sensed auditory signals;
a second near field communication interface; and
a signal processor in electrical communication with the sensor and the second near field communication interface, the signal processor configured to receive the input signal from the sensor and generate a stimulation signal based on the received input signal; wherein
when the removable earplug is inserted into the ear canal, the first near field communication interface and the second near field communication interface are positioned proximate each other:
a communication link is established between the first near field communication interface and the second near field communication interface;
the rechargeable energy storage device provides electrical power to the removable earplug via the communication link; and
the signal processor is configured to communicate the stimulation signal to the implantable subsystem via the communication link.

2. The cochlear implant system of claim 1, wherein the stimulator of the implantable subsystem is in electrical communication with the first near field communication interface such that the stimulator is configured to receive the stimulation signal received via the communication link.

3. The cochlear implant system of claim 1, wherein the first near field communication interface and the second near field communication interface are coils of wire.

4. The cochlear implant system of claim 1, further comprising an implanted charging coil in electrical communication with the rechargeable energy storage device and configured to receive electrical energy from an external device and provide electrical charge to the rechargeable energy storage device.

5. The cochlear implant system of claim 4, further comprising an external device configured to wirelessly provide electrical power to the implanted charging coil to charge the rechargeable energy storage device.

6. The cochlear implant system of claim 4, wherein the rechargeable energy storage device and the implanted charging coil are housed in a single housing.

7. The cochlear implant system of claim 6, wherein the stimulator is housed within the single housing and the cochlear electrode extends from the single housing.

8. The cochlear implant system of claim 7, wherein the first near field communication interface is housed within the single housing.

9. The cochlear implant system of claim 1, wherein the sensor comprises a microphone.

10. The cochlear implant system of claim 1, wherein the rechargeable energy storage device does not output electrical energy until the first near field communication interface and the second near field communication interface are in wireless communication with each other.

11. The cochlear implant system of claim 1, wherein the signal processor of the removable earplug comprises a first signal processor, and wherein the implantable subsystem comprises an implanted signal processor in electrical communication with the first near field communication interface, the implanted signal processor being programmed with a transfer function and being configured to:
receive the stimulation signal from the first signal processor when the first near field communication interface and the second near field communication interface are in wireless communication with each other; and output a modified stimulation signal to the stimulator based on the received stimulation signal and the transfer function.

12. The cochlear implant system of claim 1, wherein the removable earplug does not contain a power source.

13. The cochlear implant system of claim 1, wherein the rechargeable energy storage device is configured to be implanted in a head of a person.

14. The cochlear implant system of claim 1, wherein the rechargeable energy storage device has a capacity of at least 3.5 Watt-hours.

15. A cochlear implant system comprising:
a removable earplug configured to be inserted into an ear canal comprising:
a sensor configured to receive auditory signals and generate an input signal representative of the received auditory signals;
a signal processor in electrical communication with the sensor configured to receive signals from the sensor and output a stimulation signal; and
a near field communication interface in electrical communication with the sensor and the signal processor; and
wherein the removable earplug does not include a power source and is configured to:
receive electrical power via the near field communication interface; and
output the stimulation signal from the signal processor via the near field communication interface.

16. The cochlear implant system of claim 15, further comprising:
a cochlear electrode comprising a plurality of contact electrodes;
a stimulator in electrical communication with the cochlear electrode;
a rechargeable energy storage device in electrical communication with the stimulator; and
an implanted near field communication interface implanted subcutaneously, proximate the ear canal, in electrical communication with the rechargeable energy storage device and the stimulator; wherein
when the removable earplug is inserted into the ear canal such that the near field communication interface and the implanted near field communication interface are aligned, the rechargeable energy storage device provides power to the removable earplug through the aligned near field communication interfaces and the signal processor of the removable earplug outputs the stimulation signal to the stimulator through the aligned near field communication interfaces.

17. The cochlear implant system of claim 16, wherein the near field communication interface and implanted near field communication interface each comprise a coil.

18. The cochlear implant system of claim 16, further comprising a charging coil in electrical communication with the rechargeable energy storage device, wherein the charging coil is configured to receive electrical energy from an external charging device and provide electrical energy to the rechargeable energy storage device.

19. A method of operating a cochlear implant system comprising:
implanting a cochlear electrode, a stimulator, and a rechargeable energy storage device into a person and further implanting a first near field communication interface proximate an ear canal of the person, the stimulator in electrical communication with the cochlear electrode and the first near field communication interface and the rechargeable energy storage device in electrical communication with the first near field communication interface; and
inserting a removable earplug comprising a sensor, a signal processor, and a second near field communication interface, the signal processor in electrical communication with the sensor and the second near field communication interface, into the ear canal such that the second near field communication interface is aligned with the first near field communication interface provides electrical power to the removable earplug from the rechargeable energy storage device via the first near field communication interface and the second near field communication interface.

20. The method of claim 19, wherein the signal processor of the removable earplug is configured to receive an input signal from the sensor and transform the input signal into a stimulation signal by applying a transfer function to the input signal.

21. The method of claim 19, further comprising:
implanting a signal processor in the person, the signal processor in electrical communication with the first near field communication interface, the implanted signal processor being programmed with a transfer function; wherein
the implanted signal processor is configured to:
receive a signal from the removable earplug via the first and second near field communication interface;
generate a stimulation signal based on the transfer function and the received signal; and
output the stimulation signal to the stimulator to stimulate the cochlear electrode.

22. The method of claim 21, wherein:
the signal processor of the removable earplug is configured to:
generate a first stimulation signal based on an input signal received from the sensor of the removable earplug; and
output the first stimulation signal via the second near field communication interface; and
the implanted signal processor is configured to receive the first stimulation signal via the first near field communication interface such that:
the receiving the signal from the removable earplug comprises receiving the first stimulation signal;
the generating the stimulation signal based on the transfer function and received signal comprises generating a modified stimulation signal; and
the outputting the stimulation signal to the stimulator comprises outputting the modified stimulation signal.

* * * * *